US00PP34866P2

(12) United States Plant Patent
Bozanic Tanjga

(10) Patent No.: US PP34,866 P2
(45) Date of Patent: Dec. 27, 2022

(54) ***ROSA* PLANT NAMED 'BOZFRA121'**

(50) Latin Name: *Rosa hybrida*
Varietal Denomination: BOZFRA121

(71) Applicant: Biljana Bozanic Tanjga, Novi Sad (RS)

(72) Inventor: Biljana Bozanic Tanjga, Novi Sad (RS)

(73) Assignee: Pheno Geno Roses B.V.

( * ) Notice: Subject to any disclaimer, the term of this patent is extended or adjusted under 35 U.S.C. 154(b) by 0 days.

(21) Appl. No.: 17/736,589

(22) Filed: May 4, 2022

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./103
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Rosa* plant named 'BOZFRA121' is disclosed, characterized by large, white double flowers with yellow centers. Blooms profusely from May to September. Plants are tolerant to rust and downy mildew. The new variety is a *Rosa*, normally produced as an outdoor garden or container plant.

2 Drawing Sheets

Figure 1:
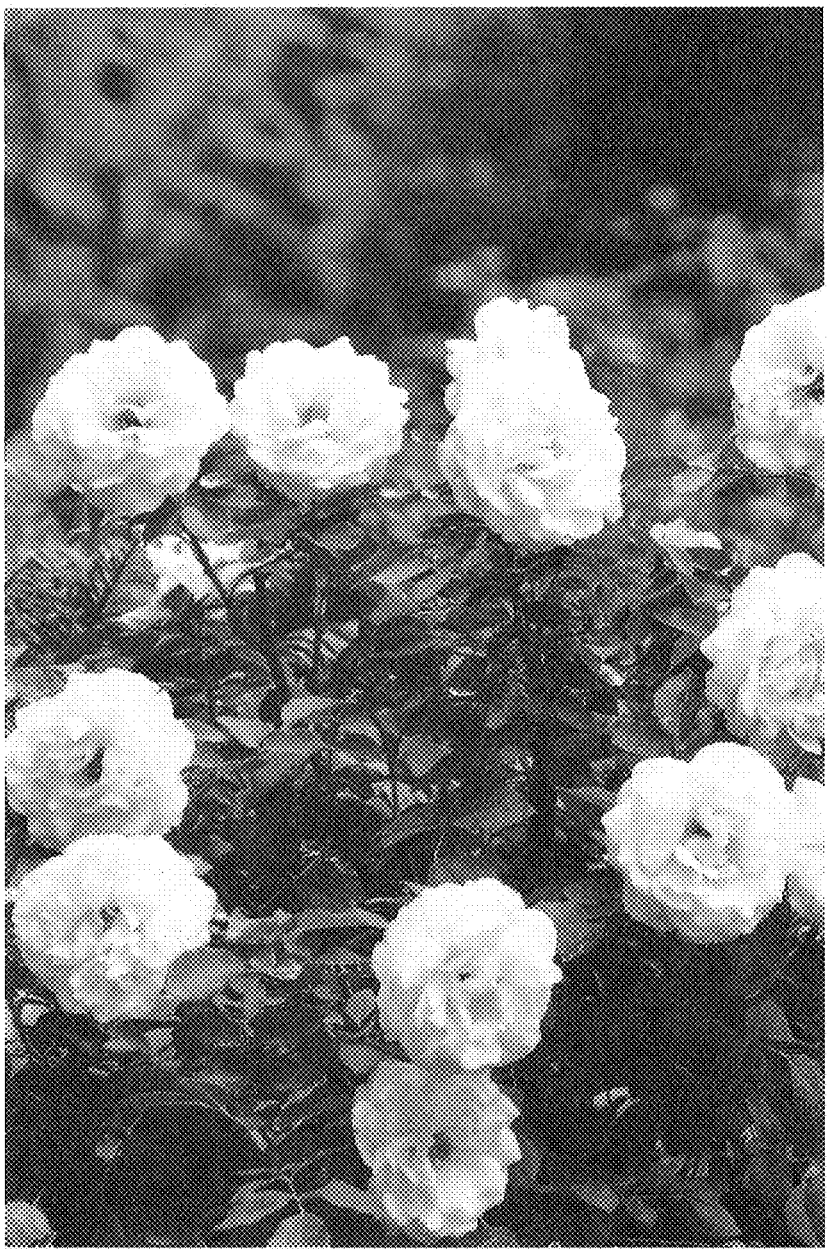

Latin name of the genus and species: *Rosa hybrida*.
Variety denomination: 'BOZFRA121'.

BACKGROUND OF THE INVENTION

The new *Rosa* cultivar is a product of a planned breeding program conducted by the inventor, Biljana Bozanic Tanjga, in Temerin, Serbia. The objective of the breeding program was to produce new profusely flowering shrub rose plants with good disease resistance, and large, vibrantly colored blooms. The cross resulting in this new variety was made during May of 2010.

The seed parent is *Rosa* 'KORPRIGGOS', U.S. Plant Pat. No. 21,314. The pollen parent is the unpatented *Rosa* 'Irish Hope'. The new variety was discovered in June of 2011 by the inventor in a group of seedlings resulting from the 2010 crossing, in a research nursery in Temerin, Serbia.

Asexual reproduction of the new cultivar was performed by softwood cuttings at a research nursery in Mali Idjos, Serbia in 2012, and has shown that the unique features of this cultivar are stable and reproduced true to type in multiple successive generations

SUMMARY OF THE INVENTION

The cultivar *Rosa* 'BOZFRA121' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BOZFRA121'. These characteristics in combination distinguish 'BOZFRA121' as a new and distinct *Rosa* cultivar:

1. White flowers with a yellow center.
2. Double flowers with a rounded shape, and a flat profile of lower and upper parts.

3. Blooms profusely from May to September.
4. Semi-upright habit.
5. Tolerant to rust and downy mildew.

Plants of the new cultivar 'BOZFRA121' are similar to plants of the seed parent in most horticultural characteristics, however, plants of the new cultivar 'BOZFRA121' differ in the following;

1. Plants of the new variety are not as tall as plants of the seed parent.
2. Flowers of the new variety have fewer petals than flowers of the seed parent.
3. Flowers of the new variety are larger than flowers of the seed parent.
4. The new variety has more flowering laterals than the seed parent.

Plants of the new cultivar 'BOZFRA121' are similar to plants of the pollen parent in most horticultural characteristics, however, plants of the new cultivar 'BOZFRA121' differ in the following;

1. Plants of the new variety are not as tall as plants of the pollen parent.
2. Flower color of the new variety is white with a yellow center, while the flower color of the pollen parent is light yellow.
3. Flowers of the new variety have a very mild fragrance, while flowers of the pollen parent have a lemony fragrance.
4. Flowers of the new variety are larger than flowers of the pollen parent.

COMMERCIAL COMPARISON

Plants of the new cultivar 'BOZFRA121' are comparable to the commercial variety *Rosa* 'Windermere', unpatented. The two *Rosa* varieties are similar in most horticultural characteristics; however, the new variety 'BOZFRA121' differs in the following:

1. Flowers of the new variety are more flat, while flowers of this comparator are more cupped.
2. Flower petal margins of the new variety are more crenated, while flower petal margins of this comparator are more entire, less undulate.
3. Flower centers of the new variety are somewhat more visible than flower centers of this comparator.
4. Flowers of the new variety have a lighter fragrance than flowers of this comparator.
5. The new variety has a more compact growth habit than this comparator.

BRIEF DESCRIPTION OF THE PHOTOGRAPHS

The accompanying photograph in FIG. 1 illustrates in full color a typical plant of 'BOZFRA121' grown in a 2-gallon container. Age of the plant photographed is approximately 5 months.

Figure 2:
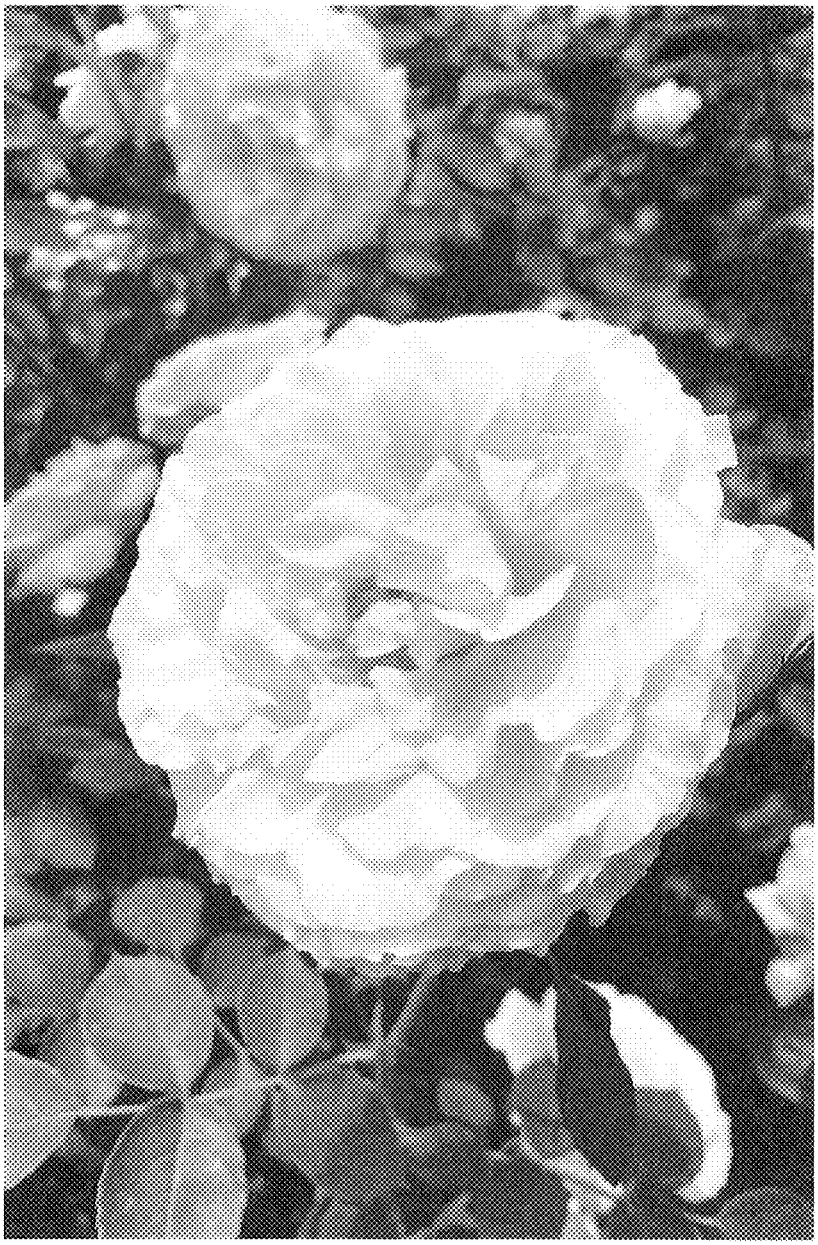

FIG. 2 illustrates a close-up view of flowers of 'BOZFRA121'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BOZFRA121' plants grown outdoors during the Spring and Summer, in Grand Haven, Mich. The growing temperature ranged from 15° C. to 40° C. during the day and from −25° C. to 30° C. during the night. General light conditions were bright, normal sunlight. No chemical treatments were used. Measurements and numerical values represent averages of typical plant types.

Botanical classification: *Rosa* 'BOZFRA121'.

PROPAGATION

Propagation method: Softwood cuttings.
Time to initiate roots: 30 days at 20° C. in summer.
Time to produce rooted plant: 120 days at 20° C. in summer.
Root description: Good density, moderately branched, medium thickness, fibrous, and fleshy. White in color, not accurately measured using R.H.S. chart.

PLANT

Age of plant described: Approximately 2 years old.
Plant type: Perennial shrub.
Growth habit: Upwards and outwards.
Plant shape: Upright and somewhat spreading.
Height: 50 cm.
Plant spread: 65 cm.
Growth rate: Moderate.
Plant vigor: Good.
Branching characteristics: Basal.
Length of primary lateral branches: 45 cm.
Diameter of lateral branches: 5 mm.
Quantity of lateral branches: 20 to 25.
Internode length: 4 cm.
Stem:
- *Shape*.—Round.
- *Aspect*.—Upright, slightly drooping.
- *Strength*.—Good.
- *Color*.—RHS Yellow-Green 144A.
- *Pubescence*.—None.

Thorns:
- *Quantity*.—2 to 3 per linear cm.
- *Shape*.—Narrow, bent downward.
- *Apex*.—Acicular.
- *Base*.—Obtuse.
- *Height*.—6 cm.
- *Color, immature*.—RHS Greyed-Purple 184B.
- *Color, mature*.—RHS Greyed-Purple 184B.

FOLIAGE

Leaf:
- *Arrangement*.—Alternate.
- *Quantity*.—5 to 10 per lateral branch.
- *Length*.—14 cm.
- *Width*.—10 cm.

Leaflet:
- *Quantity*.—5 per leaf.
- *Terminal length*.—6 cm.
- *Terminal width*.—3.5 cm.
- *Lateral length*.—5 cm.
- *Lateral width*.—3 cm.
- *Shape of blade*.—Elliptic.
- *Apex*.—Acuminate.
- *Base*.—Obtuse.
- *Margin*.—Serrulate.
- *Texture*.—Coriaceous upper surface, glabrous lower surface.
- *Pubescence*.—None.
- *Glossiness*.—Very weak.
- *Color*.—Young foliage upper side: RHS Green 137B. Young foliage under side: RHS Green 138B. Mature foliage upper side: RHS Green NN137A. Mature foliage under side: RHS Yellow-Green 147B.
- *Venation*.—Type: Pinnate. Venation color upper side: RHS Yellow-Green 144C. Venation color under side: RHS Yellow-Green 144C.

Petiole:
- *Leaf*.—Length: 3 cm. Diameter: 2 mm. Color, upper surface: RHS Yellow-Green 144C. Color, lower surface: RHS Yellow-Green 144C. Texture: Glabrous.
- *Leaflet*.—Length: 2 mm. Diameter: 1 mm. Color, upper surface: RHS Yellow-Green 144C, with tinges of Greyed-Red 179C. Color, lower surface: RHS Yellow-Green 144C. Texture: Glabrous.

Stipules:
- *Quantity*.—2.
- *Shape*.—Linear to acicular.
- *Apex*.—Acicular.
- *Base*.—Fused along petiole.
- *Margin*.—Ciliate.
- *Length*.—1.5 cm.
- *Width*.—2 mm.
- *Texture*.—Smooth, both surfaces.
- *Color, upper surface*.—RHS Green NN137A.
- *Color, lower surface*.—RHS Yellow-Green 147B.

FLOWER

Natural flowering season: Spring through summer.
Flower type and habit: 1 to 4 blooms arranged terminally on lateral branches.

Flower form: Double flower, whorled.
*Shape*.—Round whorl.
*Diameter*.—12 cm.
*Depth*.—5.5 cm.
*Aspect*.—Upright.
*Persistent or self-cleaning*.—Self-cleaning.

Bud:
*Shape*.—Ovate.
*Length*.—2 cm.
*Diameter*.—1.5 cm.
*Color*.—RHS Yellow-Green 144A.

Petals:
*Arrangement*.—Double whorl.
*Appearance*.—An abundance of recurve petals with a rounded appearance and slightly curling margins.
*Length*.—Outer whorl: 6 cm. Inner whorl: 4 cm.
*Width*.—Outer whorl: 5 cm. Inner whorl: 3 cm.
*Shape*.—Outer whorl: Orbicular. Inner whorl: Obovate.
*Margin*.—Entire to slightly crenate.
*Apex*.—Obtuse to retuse.
*Fused*.—No.
*Quantity*.—About 50.
*Texture*.—Silky and smooth.
*Color*.—When opening: Upper surface: RHS Yellow-Orange 16D, fading to Yellow 9C at base. No distinctive basal spot. Lower surface: RHS Yellow-Orange 16D. No distinctive basal spot. Fully opened: Upper surface: RHS White 155A, fading to Yellow 8A at base. No distinctive basal spot. Lower surface: RHS White 155A, fading to Yellow 8A at base. No distinctive basal spot.

Petaloids:
*Shape*.—Irregular, wrinkled.
*Arrangement*.—Whorled.
*Quantity*.—15 to 20.
*Margin*.—Slightly crenate.
*Length*.—3 cm.
*Width*.—1.5 cm.
*Color*.—Immature: RHS White 155A, fading to Yellow 8A at base. Mature: RHS White 155A, fading to Yellow 8A at base.

Sepals:
*Appearance*.—Rough, recurved toward stem.
*Arrangement*.—Whorl around base.
*Quantity*.—5.
*Shape*.—Triangular.
*Margin*.—Entire.
*Apex*.—Aristate.
*Sepal extensions*.—Absent.
*Base*.—Fused.
*Length*.—3 cm.
*Width*.—1 cm.
*Texture*.—Rough and somewhat pubescent.
*Color*.—Immature, upper side: RHS Yellow-Green 144A. Immature, under side: RHS Yellow-Green 144A. Mature, upper side: RHS Yellow-Green 144A. Mature, under side: RHS Yellow-Green 144A.

Calyx:
*Shape*.—Collar-like with recurved sepals arranged in a whorl.
*Length*.—2 cm.
*Diameter*.—1.5 cm.

Peduncle:
*Length*.—4 cm.
*Diameter*.—3 mm.
*Angle*.—Upright, 75 to 90°.
*Strength*.—Strong.
*Texture*.—Slightly prickly.
*Color*.—RHS Yellow-Green 144A, with tinges of Greyed-Red 179C.

Fragrance: Faintly sweet fragrance.

REPRODUCTIVE ORGANS

Stamens:
*Number*.—About 130.
*Filament color*.—RHS Yellow-Orange 16A.

Anthers:
*Length*.—2 mm.
*Shape*.—Club-like, basifixed.
*Color*.—RHS Yellow-Orange 17A.
*Pollen*.—None.

Pistil:
*Number*.—85.
*Length*.—10 mm.
*Style*.—Length: 9 mm. Color: RHS Green-Yellow 1C.
*Stigma*.—Shape: Rounded, flat-topped. Color: RHS Yellow 4B.
*Receptacle*.—Height: 1.5 cm. Diameter: 1 cm. Shape: Orbicular. Texture: Glabrous. Color: RHS Green 143C.

OTHER CHARACTERISTICS

Seeds and fruits: None observed.
Disease/pest resistance: Tolerant to rust (various species of *Phragmidium*) and downy mildew (*Peronospora sparsa*).
Temperature tolerance: Observed tolerance between −25° C. to at least 40° C. degrees.

What is claimed is:

1. A new and distinct cultivar of *Rosa* plant named 'BOZFRA121' as herein illustrated and described.

* * * * *